(12) United States Patent
Riviere

(10) Patent No.: US 7,816,078 B2
(45) Date of Patent: Oct. 19, 2010

(54) METHOD FOR IDENTIFYING BIOLOGICAL SPECIES

(75) Inventor: Marcos Isamat Riviere, Barcelona (ES)

(73) Assignee: Laboratorios Dr. F. Echevarne, Analisis, S.A., Barcelona (ES)

( * ) Notice: Subject to any disclaimer, the term of this patent is extended or adjusted under 35 U.S.C. 154(b) by 818 days.

(21) Appl. No.: 10/577,393

(22) PCT Filed: Oct. 27, 2003

(86) PCT No.: PCT/ES03/00547

§ 371 (c)(1), (2), (4) Date: Apr. 27, 2006

(87) PCT Pub. No.: WO2005/040423

PCT Pub. Date: May 6, 2005

(65) Prior Publication Data

US 2007/0048739 A1   Mar. 1, 2007

(51) Int. Cl.
C12Q 1/68 (2006.01)
C07H 21/04 (2006.01)
(52) U.S. Cl. .................. 435/6; 536/24.31; 536/23.1
(58) Field of Classification Search .................. 435/6; 536/24.31, 23.1
See application file for complete search history.

(56) References Cited

U.S. PATENT DOCUMENTS 5,645,994 A   7/1997   Huang

OTHER PUBLICATIONS

Lockley et al., "Intron variability in an actin gene can be used to discriminate between chicken and turkey DNA," Meat Sci 61:163-168, 2002.*

Nakajima-Iijima et al., "Molecular structure of the human cytoplasmic β-actin gene: interspecies homology of sequences in the introns,"PNAS 82:6133-6137, 1985.*
du Breuil et al., "Quantitation of beta-actin-specific mRNA transcripts using xeno-competitive PCR," Genome Res 3:57-59, 1993.*
Sambrook et al., Molecular Cloning, A Laboratory Manual, 2d ed., Cold Spring Harbor Laboratory Press, Plainview, New York, 1989, chap. 6, pp. 30-33, and chap. 14, pp. 5, 10 and 11.*
Bellis, C. et al., A molecular genetic approach for forensic animal species identification, Forensic Science International, 134 99-108 (2003).
Kocher T.D. et al., Dynamics of mitochondrial DNA evolution in animals: Amplification and sequencing with conserved primers, Proc. National Academy of Science U.S.A., vol. 86 6196-6200 (1989).
Rodriguez, M.A. et al., Qualitative PCR for the detection of chicken and pork adulteration in goose and mule duck foie grass, Journal of the Science of Food and Agriculture 83: 1176-1181 (2003).
NG, S.-Y. et al., Evolution of the Functional Human β-Actin Gene and Its Multi-Pseudogene Family: Conservation of Noncoding Regions and Chromosomal Dispersion of Pseudogenes, Molecular and Cellular Biology vol. 5, No. 10, 2720-2732 (1985).

* cited by examiner

Primary Examiner—Karen Cochrane Carlson
Assistant Examiner—Rosanne Kosson
(74) Attorney, Agent, or Firm—Gottlieb, Rackman & Reisman, P.C.

(57) ABSTRACT

The present invention provides a method for identifying species and subspecies in a biological sample through the selective amplification of segments of nucleic acid that code a target region of the cytoplasmatic beta-actin protein, which is present in all the organisms concerned. The method comprises DNA extraction from the sample; amplification of divergent segments of the cytoplasmatic beta-actin gene by PCR or an equivalent technique, using primers of regions with high evolutionary conservation between species and subspecies; and identification of the amplified segment by comparison of its size in base pairs with a pre-established standard of sizes and/or identification of the amplified segment by DNA sequencing and comparison of the resulting sequence with the specific sequence of each species or subspecies present on a computer database.

6 Claims, 8 Drawing Sheets

SEQ ID No. 1 (1132-1151)   5'-TCCGGCATGTGCAAGGCCGG-3'
SEQ ID No. 2 (1474-1454)   5'-CTCCATGTCGTCCCAGTTGG-3'

SEQ ID No. 3 (1453-1484)   5' ACCAACTGGGACGACATGGAGAAGATCTGGC 3'
SEQ ID No. 4 (2063-2034)   5' TACATGGCNGGGGTGTTAAAGGTCTCAAAC 3'

SEQ ID No. 5 (2434-2463)   5' TGCCCTGAGGCCCTCTTCCAGCCTTCCTTC 3'
SEQ ID No. 6 (2681-2643)   5' GGGTACATGGTGGTGCCGCCAGACAGCACNGTGTTGGC 3'

SEQ ID No. 7 (2643-2681)   5' GCCAACACNGTGCTGTCTGGCGGCACCACCATGTACCC 3'
SEQ ID No. 8 (2952-2932)   5' TCGTACTCCTGCTTGCTGATCCACATCTG 3'

FIG. 2

FIG. 8 (SEQ ID NO:9)

```
   1 gcccagcacc caaggcggc caacgccaaa actctccctc ctcctcttcc tcaatctcgc
  61 tctcgctctt ttttttttc gcaaaaggag gggagagggg gtaaaaaaat gctgcactgt
 121 gcggcgaagc cggtgagtga gcggcgcggg gccaatcagc gtgcgccgtt ccgaaagttg
 181 ccttttatgg ctcgagcggc cgcggcggcg ccctataaaa cccagcggcg cgacgcgcca
 241 ccaccgccga gaccgcgtcc gcccgcgagc acagagcctc gccttgccg atccgcgcc
 301 cgtccacacc cgccgccagg taagcccggc cagccgaccg gggcatgcgg ccgcggccct
 361 tgcccgtgc agagccgccg tctggccgc agcggggggc gcatggggcg gaaccggacc
 421 gccgtggggg gcgcgggaga agccctggg cctccggaga tggggacac cccacgccag
 481 ttcgcaggcg cgaggccgcg ctcgggcggg cgcgctccgg gggtgccgct ctcggggcgg
 541 gggcaaccgg cggggtcttt gtctgagccg ggctcttgcc aatggggatc gcacggtggg
 601 cgcggcgtag ccccgtcag gcccggtggg ggctggggcg ccatgcgcgt gcgcgctggt
 661 cctttgggcg ctaactgcgt gcgcgctggg aattggcgct aattgcgcgt gcgcgctggg
 721 actcaatggc gctaatcgcg cgtgcgttct ggggcccggg cgcttgcgcc acttcctgcc
 781 cgagccgctg gcgcccgagg gtgtggccgc tgcgtgcgcg cgcgcgaccc ggtcgctgtt
 841 tgaaccgggc ggaggcgggg ctggcgcccg gttgggaggg ggttggggcc tggcttcctg
 901 ccgcgcgccg cggggacgcc tccgaccagt gttgcctt tatggtaata acgcggccgg
 961 cccggcttcc tttgtcccca atctgggcgc gcgccggcgc ccctggcgg cctaaggact
1021 cggcgcgccg gaagtggcca gggcggggc gacttcggct cacagcgcgc ccggctattc
1081 tgcagctca ccatggatga tgatatcgcc gcgctcgtcg tcgacaacgg ctccggcatg
1141 tgcaaggccg gcttcgcggg cgacgatgcc cccgggccg tcttcccctc catcgtgggg
1201 cgccccaggc accaggtagg ggagctggct gggtggggca gccccgggag cgggcgggag
1261 gcaagggcgc tttctctgca caggagcctc ccggtttccg gggtgggctg cgcccgtgct
1321 cagggcttct tgtccttcc ttcccaggac gtgatggtgg gcatgggtca gaaggattcc
1381 tatgtgggcg acgaggccca gagcaaggaga ggcatcctca ccctgaagta ccccatcgag
1441 cacggcatcg tcaccaactg ggacgacatg gagaaaatct ggcaccacac cttctacaat
1501 gagctgcgtg tggctcccga ggagcacccc gtgctgctga ccgaggcccc cctgaacccc
1561 aaggccaacc gcgagaagat gacccaggtg agtggcccgc tacctcttct ggtggccgcc
1621 tccctccttc ctggcctccc ggagctgcgc cctttctcac tggttctctc ttctgccgtt
1681 ttccgtagga ctctcttctc tgacctgagt ctccttggga actctgcagg ttctatttgc
1741 tttttcccag atgagctctt tttctggtgt ttgtctctct gactaggtgt ctgagacagt
1801 gttgtgggtg taggtactaa cactggctcg tgtgacaagg ccatgaggct ggtgtaaagc
1861 ggccttggag tgtgtattaa gtaggcgcac agtaggtctg aacagactcc ccatcccaag
1921 accccagcac acttagccgt gttctttgca cttctgcat gtccccgtc tggcctggct
1981 gtccccagtg gcttccccag tgtgacatgg tgcatctctg ccttacagat catgtttgag
2041 accttcaaca ccccagccat gtacgttgct atccaggctg tgctatccct gtacgcctct
2101 ggccgtacca ctggcatcgt gatggactcc ggtgacgggg tcaccacac tgtgcccatc
2161 tacgagggt atgccctccc ccatgccatc ctgcgtctgg acctggctgg ccgggacctg
2221 actgactacc tcatgaagat cctcaccgag cgcggctaca gcttcaccac cacggccgag
2281 cgggaaatcg tgcgtgacat taaggagaag ctgtgctacg tgccctgga cttcgagcaa
2341 gagatggcca cggctgcttc cagctcctcc ctggagaaga gctacgagct gcctgacggc
2401 caggtcatca ccattggcaa tgagcggttc cgctgccctg aggcactctt ccagccttcc
2461 ttcctgggtg agtggagact gtctcccggc tctgctgac atgagggtta ccctcgggg
2521 ctgtgctgtg gaagctaagt cctgccctca tttccctctc aggcatggag tcctgtggca
2581 tccacgaaac taccttcaac tccatcatga agtgtgacgt ggacatccgc aaagacctgt
2641 acgccaacac agtgctgtct ggccgcacca ccatgtaccc tggcattgcc gacaggatgc
2701 agaaggagat cactgccctg gcacccagca caatgaagat caaggtgggt gtctttcctg
2761 cctgagctga cctgggcagg tcagctgtgg ggtcctgtgg tgtgtgggga gctgtcacat
2821 ccagggtcct cactgcctgt ccccttcct cctcagatca ttgctcctcc tgagcgcaag
2881 tactccgtgt ggatcggcgg ctccatcctg gcctcgctgt ccaccttcca gcagatgtgg
2941 atcagcaagc aggagtatga cgagtccggc ccctccatcg tccacgcaa atgcttctag
3001 gcggactatg acttagttgc gttacaccct ttcttgacaa aacctaactt gcgcagaaaa
3061 caagatgaga ttggcatggc tttatttgtt tttttgttt tgtttggtt ttttttttt
3121 ttttggcttg actcaggatt taaaaactgg aacggtgaag gtgacagcag tcggttggag
3181 cgagcatccc ccaaagttca caatgtggcc gaggactttg attgcattgt tgttttttta
3241 atagtcattc caaatatgag atgcattgtt acaggaagtc ccttgccatc ctaaaagcca
3301 ccccacttct ctctaaggag aatgggccag tcctctccca agtccacaca ggggaggtga
3361 tagcattgct ttcgtgtaaa ttatgtaatg caaaattttt ttaatcttcg ccttaatact
3421 tttttatttt gttttatttt gaatgatgag ccttcgtgcc cccccttccc cctttttgtc
3481 ccccaacttg agatgtatga aggcttttgg tctccctggg agtgggtgga ggcagccagg
3541 gcttacctgt acactgactt gagaccagtt gaataaaagt gcacactta aaaatgaggc
3601 caagtgtgac tttgtggtgt ggctgggttg ggggcagcag agggtg
```

METHOD FOR IDENTIFYING BIOLOGICAL SPECIES

The present invention relates to the field of taxonomic analysis of biological samples, based on the use of the DNA sequence of a highly evolutionarily conserved protein.

PRIOR ART

The taxonomic analysis of samples is applicable to a broad spectrum of industries and activities. The three main areas of application of taxonomic analysis are:

Analysis of Foodstuffs and Monitoring of Food Production Chains

The demand for tests that provide traceability of the taxonomic origin of biological samples or foodstuffs has increased since the crisis in the food sector triggered by the epidemiological outbreak of Bovine Spongiform Encephalopathy in the United Kingdom and the growing tendency to illegally mix meats of different taxonomic origins, without labelling the end product accordingly. For example, it has been disclosed that meat of bovine origin had been systematically added to chicken products imported to Holland from all over the world and then distributed across Europe. Other forms of adulteration have also been reported and it is believed that the practice may be widespread in industries within this sector. However, it is difficult to detect without developing advanced techniques based on DNA analysis.

Safety tests on foodstuffs are normally conducted in government laboratories, food processing plants and service companies associated with these industries. At present, users of this sector are increasingly seeking methods of control in response to growing customer demands. In this respect, certain supermarket chains have established partnerships with technological firms in order to develop methods of tracing the taxonomic origin of meat products using genetic techniques.

In a related application, the analysis of animal feed is one of the priorities of the European Agricultural Agenda, particularly after the "mad cow" crisis concerning animal feed. The analysis of foodstuffs is highly desirable and could be made compulsory in the near future. Monitoring procedures are currently based on keeping records but they do not cover the practices of illegal adulteration or dilutions that are carried out indiscriminately in many parts of the world.

Monitoring and Surveillance of Biodiversity

Biodiversity is the result of the interactions between the phylogenetic history of life on earth and evolutionary processes. As such, biodiversity is the sum of all life on earth and it includes genetic and functional diversity and the diversity of species.

One of the first steps in biodiversity monitoring programmes is the compilation of a taxonomic inventory, specifying all the taxa and their systematics in a specific ecosystem that includes animals, plants and microorganisms. These inventories provide the basis for all monitoring of biodiversity and conservation programmes. Global biodiversity is extremely vast: 52,629 different species of vertebrates, 4.63 million species of invertebrate and 265,876 species of plants and fungi have so far been described (figures taken from the Red List).

DNA is increasingly being accepted as the means of monitoring biodiversity. For example, DNA taken from the fur found in Canadian forests in 2002 was used to confirm that the Wild lynx still exists in the region of the great lakes.

Monitoring and Surveillance of Endangered Species.

There are currently about 8,000 animal and plant species on official lists of endangered species, and this figure is rising each year. This trend points to the need for straightforward, "universally" usable tests for identifying the taxonomic origin of biological samples.

The trade of products made from endangered species is controlled by the, Convention on International Trade in Endangered Species of Wild Fauna and Flora (CITES) and DNA tests are currently being developed under the sponsorship of this organisation to monitor this illegal trade. It is particularly important to be able to detect processed animal or plant products, such as foodstuffs or cosmetics, far more so than animal-derived raw materials such as furs, which do not require DNA testing for their identification. An example of this is the use of powdered tiger's teeth, which is widely used in traditional medicines, despite it having been declared that the survival of the species is in a grave state of danger. DNA testing has been used to identify the tiger-derived material based on the gene sequence of cytochrome b in amplified DNA and similar tests have been disclosed to trace whale meat from protected groups in processed products that apparently contain "legal" whale meat. Similar approaches have been applied to protected orchids, snakes and crocodiles in products destined for human consumption and the origin of caviar from protected sturgeons, etc. It is very likely that the use of this type of technologies for monitoring endangered species will become much more widespread in the near future.

Technology Applied to the Taxonomic Analysis of Samples

The methodology used to determine the animal origin of biological samples derives primarily from the food industry and the meat product sector. From the traditional methods based on electrophoretic and/or immunochemical analysis of proteins, technology has progressed towards the analysis of the DNA content of food samples in order to unequivocally identify the nature of the product. These methods identify nucleic acids through the hybridisation of specific probes for a specific species and/or the selective amplification of the target sequences using polymerase chain reaction (PCR).

The amplification has targeted segments of mitochondrial DNA (cfr. Bartlett et al. *BioTechniques* 1992 vol. 12 pp. 408-411; Unseld et al. *Genome Research* 1995 vol. 4 pp. 241-243; Palumbi et al. *J. Hered.* 1998 vol. 89 pp. 459-464; Wolf et al. *J. Agricult and Food Chem.* 1999 vol. 47 pp. 1350-1355; Partis et al. *Meat Science* 2000 vol. 54 pp. 369-376 ). This method is not suitable for determining samples with a dual or heterogeneous taxonomic origin. The amplification has also targeted nuclear DNA (cfr. Janssen et al. *J. Ind. Microbiol. and Biotech.* 1998 vol. 21 pp. 115-120, Matsunaga et al. *Meat Science* 1999 vol. 51 pp. 143-148; Wolf and Lüthy *Meat Science* 2001 vol. 57 pp. 161-168). Some of the most important proteins have been type II DNA-Topoisomerase (cfr. U.S. Pat. No. 5.645.994) and α-cardiac actin (cfr. Bartlett et al. *Meat Science* 1998 vol. 50 pp. 105-114; Fairbrother et al. *Animal Biotech.* 1998 vol. 9 pp. 89-100; Lockley and Bardsley *Meat Science* 2002 vol. 61 pp. 163-168).

Some methods are based on a PCR where one oligonucleotide primer is generic and the other is dependent on the species to be identified, which is of some use in the identification of widely consumed meat species (cfr. Matsunaga et al. *Meat Science* 1999 vol. 51 pp. 143-148). Other methods have been designed to confirm the presence of DNA deriving from porcine (cfr. Montiel-Sosa et al. *J. Agric. Food Chem.* 2000 vol. 48 pp. 2829-2832), bovine, ostrich and emu species (cfr. Colombo et al. *Meat Science* 2000 vol. 56 pp. 15-17) in biological samples, but the problem arises when its presence fails to be confirmed, as this technology does not provide data on the taxonomic identity of the sample analysed.

The closest document to the present invention is U.S. Pat. No. 5,645,994, which discloses a method for selectively amplifying DNA segments from one or more organisms in a sample through the use of gene sequences of type II DNA-Topoisomerase.

However, at present, all these methods are of limited use when the sample comprises a mixture of organisms. They would only confirm the presence of a pre-known or suspected organism and they would not make it possible to identify each of the organisms present in the sample.

It is desirable to find a way of identifying a plurality of organisms in a single sample without having to use multiple probes and without prior knowledge of the organisms that might be present. Another aspect that could be improved is the ability to distinguish very similar or interrelated species.

DEFINITIONS

The following definitions are provided for the purposes of the present description:

Ubiquitous protein: proteins with a similar structure and function that are present in many or all of the organisms. A protein with these characteristics will be the same as the equivalent protein of the other species.

Conserved segment: Used to refer to amino acid segments and nucleotide segments. Presenting segments that are substantially or wholly common to the different species. The "high" degree of conservation indicates that the proportion of segments that several species have in common is high. This is referred to as consensus sequence.

Divergent segment: Used to refer to both amino acid segments and nucleotide segments. Presenting segments that are substantially different between different species. In this document the term "target" will also be used to refer to these sequences.

EXPLANATION OF THE INVENTION

The present invention overcomes many of the aforementioned limitations. In this regard, the inventors of the present invention have surprisingly found that the gene that codes the cytoplasmic beta-actin protein and its derived products can be applied to taxonomic identification using samples of biological material deriving from a single species or a heterogeneous mixture of species and/or subspecies.

The present invention provides a method for identifying species and subspecies in a biological sample deriving from a single species or a heterogeneous mixture of species and/or subspecies, by means of the selective amplification of nucleic acid segments that code a target region of a macromolecule present in all the organisms concerned, for which, according to a first aspect, the object of the present invention is a method comprising a step whereby DNA is extracted from the sample; a step whereby cytoplasmic beta-actin gene segments are amplified by PCR or an equivalent technique; and a step whereby the amplified segment is identified by comparing its size in base pairs with a pre-established standard of sizes and/or identifying the amplified segment by DNA sequencing and comparison of the resulting sequence with the specific sequence of each species or subspecies present on a computer database.

The step whereby the starting DNA is amplified is not restricted to use of the PCR; it is possible to use any equivalent technique that can be conducted by a person skilled in the art using the tools currently available. Likewise, for example, viewing of the PCR result is not restricted to the use of electrophoresis in agarose gel; it is also possible to use capillary electrophoresis, an automated electrophoresis or any equivalent technique with a minimum resolution that is sufficient to successfully perform the experiment.

Preferably, the regions to be amplified are divergent gene segments from the cytoplasmic beta-actin gene with DNA sequences with high evolutionary conservation between species and subspecies. And more particularly, the regions to be amplified are those which lie between the 3' sequence of the upstream exon and the 5' sequence of the downstream exon comprising the whole intronic sequence and part of the flanking exonic sequences.

In one particular embodiment of this method, the regions to be amplified are those which lie between positions 1130-1473, 1452-2063, 2438-2680 and/or 2642-2960 (numbering in relation to the DNA sequence of the human locus HUMACCYBB Accession number M10277, Genebank). In particular, the samples consist of animal tissue, more specifically horse, goat, rabbit, dog, cat, chimpanzee, human and/or brown bear tissue. In another embodiment, the samples consist of plant tissue.

In another particular embodiment of this method, in the identification step, the amplified segment or segments are compared with the human sequence M10277 and/or with the sequences of these same gene regions of species included on a computer database. The amplified segments show the conserved areas at the ends of each amplified segment and the divergence in the central region corresponding largely to the intronic region of the gene.

The present invention provides the means of identifying a plurality of organisms in a single sample without having to use multiple probes that are specific to each of the species and subspecies that might be present in the sample. The method uses universal primers, which are valid for identifying any species or subspecies present in the sample without prior knowledge of the organisms that might be present. According to the invention, a composition of universal primers are used, which hybridise with the conserved regions of the cytoplasmic beta-actin gene, preferably with the sequences which lie between positions 1130-1191 and 1453-1473; 1453-1473 and 2041-2065; 2433-2459 and 2643-2680 and/or 26432680 and 2940-2960 (numbering in relation to the DNA sequence of the human locus HUMACCYBB Accession number M10277). The particular pairs of universal primers used are (1132-1151) 5'T000GCATGTGCAAGGCCGG3' (SEQ ID NO: 1) and (1474-1454) 5'CTCCATGTCGT000AGTTGG3' (SEQ ID NO: 2); (1453-1484) 5'ACCAACTGGGACGA-CATGGAGAAGATCTGGC3' (SEQ ID NO: 3) and (2063-2034) 5'TACATGGCNGGGGTGTTAAAGGTCT-CAAAC3' (SEQ ID NO: 4), (2434-2463) 5'TGCCCTGAGGCCCTCTTCCAGCCTTCCTTC3' (SEQ ID NO: 5) and (2681-2643) 5'GGGTACATGGTGGTGC-CGCCAGACAGCACNGTGTTGGC3' (SEQ ID NO: 6); and (2643-2681) 5'GCCAACACNGTGCTGTCTGGCGGCAC-CACCATGTACCC3' (SEQ ID NO: 7) and (2952-2932) 5'TCGTACTCCTGCTTGCTGATCCACATCTG3' (SEQ ID NO: 8).

According to a second aspect, another object of the present invention is the use of DNA sequences of the cytoplasmic beta-actin gene in biological samples deriving from a single species or from a heterogeneous mixture of species and/or subspecies, to identify the biological species to which the samples belong.

The cytoplasmic beta-actin protein fulfils a number of criteria for achieving reliable identification. It is a ubiquitous protein in all the organisms concerned. cytoplasmic beta-actin is one of the six different isoforms of actin so far identified. Specifically, cytoplasmic beta-actin is one of the two non-muscular cytoskeletic actins. Its function is to allow mobility and provide the cell with structure and integrity, being a majority component of the cellular contractile apparatus. For this reason, it is a fundamental protein for the cell's survival, which means that it presents exonic segments with a high evolutionary conservation between species. The degree of equivalence in its amino acid sequence between species is between 98% and 100%, sufficient to present highly conserved segments but also divergent segments in the non-coding parts of the gene to correctly distinguish between species that are closely related to one another. The nucleotide divergence corresponding, for example, to intron B of the species being studied (1216-1347 bp, numbering in relation to DNA sequence of the human locus HUMACCYBB Accession number M10277) is less than 25%. Segments that are highly conserved between the different species and subspecies make it possible to use primers that are common to all the species and subspecies, whilst divergent segments are the object of amplification using said primers, resulting in a different pattern of amplification for each species and subspecies.

In addition to the qualitative identification of species present in an unknown sample, one aspect of the present invention relates to the quantitative analysis of the species present. This feature is important, for example, in determining the levels of contamination of a sample by material deriving from another species. In many cases, a qualitative result will be sufficient (for example, has chicken meat been adulterated using bovine products?), but in other cases a quantitative response will be necessary (how much of the bovine product has been added to the chicken meat?) This is particularly important when certain additives are accepted within specified limits.

Throughout the description and claims the word "comprise" and its variants do not imply the exclusion of other technical characteristics, additives, components or steps. The abstract of this application is included here by way of a reference.

For persons skilled in the art, other objects, advantages and characteristics of the invention will arise partly out of the description and partly when the invention is put into practice. The following particular embodiments and figures are provided by way of a non-limiting, illustrative example of the present invention.

BRIEF DESCRIPTION OF THE FIGURES

FIG. 2 shows the details of the oligonucleotide primers shown in FIG. 1. The numbering corresponds to their position on the genome sequence of the human beta-actin gene (Accession number, Genebank: M10277; Locus: HUMAC-CYBB). A: Adenine, C: Cytosine, G: Guanine: T: Thymine. N: position with nucleotide degeneration.

Cf, *Canis familiaris* (SEQ ID NO:15). Hs, *Homo sapiens* (SEQ ID NO:10). Ec, *Equus caballus* (SEQ ID NO:16). Oc, *Oryctolagus cuniculus* (SEQ ID NO:17). Rn, *Rattus norvegicus* (SEQ ID NO:18). Mm, *Mus musculus* (SEQ ID NO:11).

Figure 7:
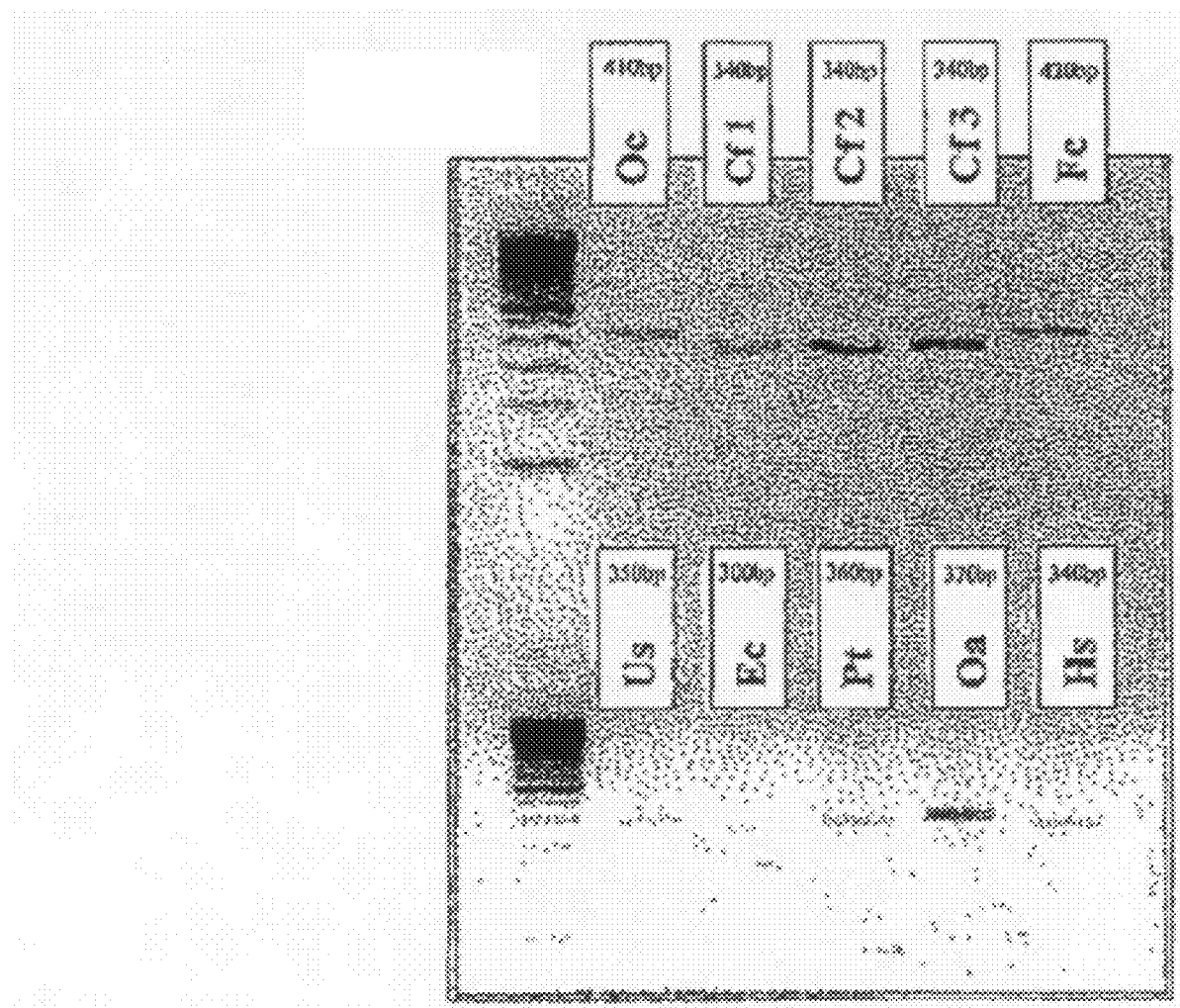

FIG. 7 shows an experimental example of an agarose gel electrophoresis corresponding to ten separate amplifications by PCR of the W region which lies between primers SEQ ID NO: 1 and SEQ ID NO: 2 of peripheral blood from eight different animal species. The numbers on each side indicate the approximate molecular weight, expressed in base pairs (bp), obtained for the W region in each of the amplifications. It is possible to observe the difference in molecular weight of this region between the animal species included. Oc: *Oryctolagus cuniculus*, rabbit. Cf: *Canis familiaris*, dog. Fc: *Felis catus*, cat. Us: *Ursus* species, Bear. Ec: *Equus caballus*, horse. Pt: *Pan troglodytes*, chimpanzee. Oa: *Ovis aries*, goat. Hs: *Homo sapiens*, man. The lanes on the left of the gel correspond to the 100 by ladder molecular weight standard (Invitrogen). In this standard, the lowest band corresponds to 100 by and as they ascend, each band is 100 by greater than the one immediately below it.

FIG. 8 sets forth the entire DNA (nucleotide) sequence of the human cytoplasmic beta-actin gene, locus HUMAC-CYBB, GenBank Accession number M10277, verison M10277.1, GI:177967.

DETAILED DESCRIPTION OF PARTICULAR EMBODIMENTS

Identification of a Species Using a Homogeneous/Heterogeneous Biological Sample.

The process developed for the taxonomic identification of a biologically heterogeneous sample of unknown composition is described below. The procedure would be the same for a homogeneous sample, as it is always presumed that absolutely nothing is known about the number of different species and/or subspecies present or the taxonomic nature in itself.

Processing the Sample

Genome DNA was extracted from a 200 µl sample of venous whole blood in EDTA, which was compatible with any commercial kit for rapid DNA extraction, for its subsequent amplification by PCR.

Figure 1:
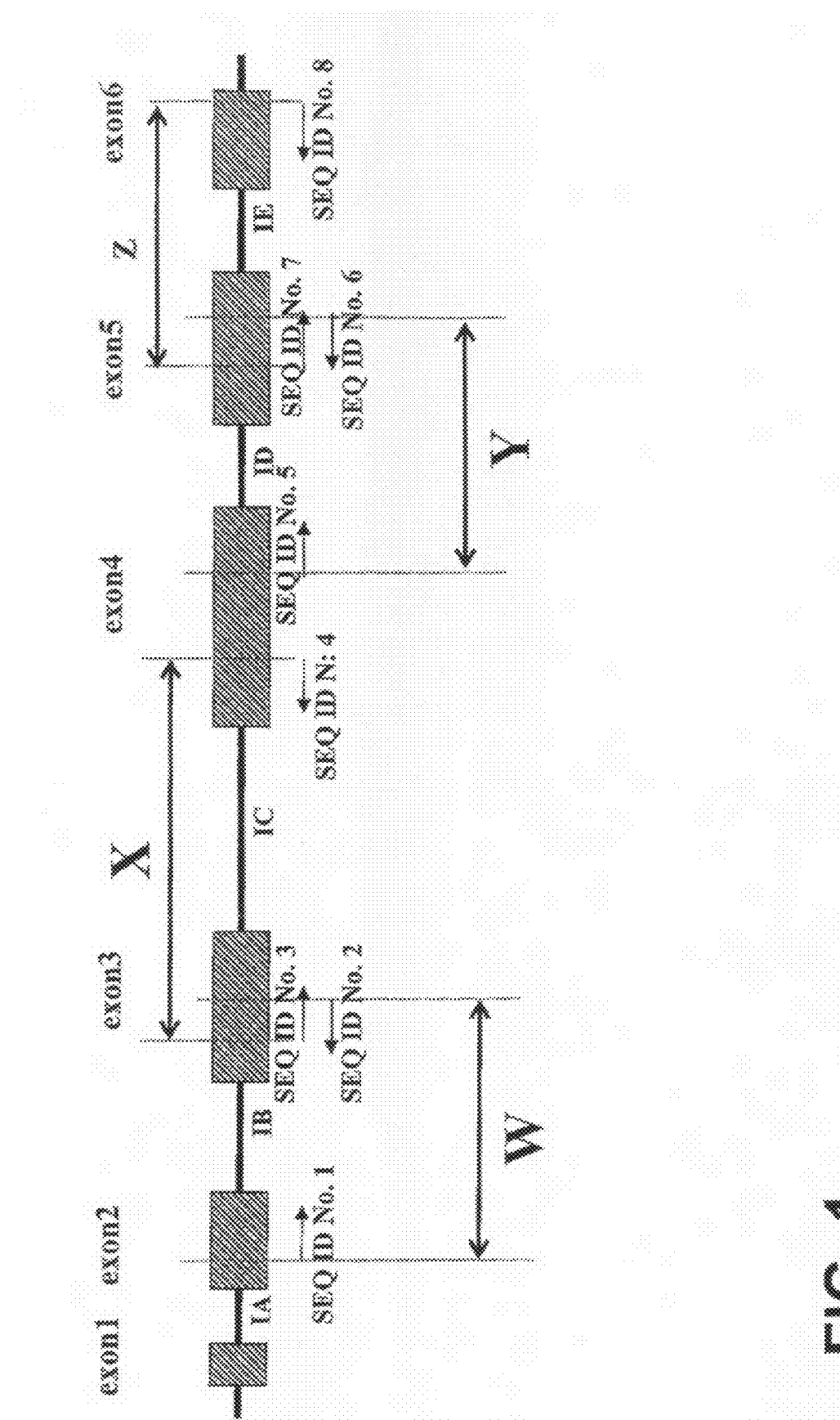
FIG. 1 shows a diagram of the structure of the human cytoplasmic beta-actin gene. The boxes represent the exons (exon 1 to 6) and the continuous black line represents the introns (I, Intron A to E). Regions W, X, Y and Z correspond to regions which lie between the pairs of primers identified herein as SEQ ID NO: 1 and SEQ ID NO: 2, SEQ ID NO: 3 and SEQ ID NO: 4, SEQ ID NO: 5 and SEQ ID NO: 6, and SEQ ID NO: 7 and SEQ ID NO: 8, respectively. These fragments (W, X, Y and Z) include DNA sequences that are divergent between different biological species and can be amplified using PCR using primers SEQ ID NO: 1 through SEQ ID NO: 8 as shown in FIG. 2.
Figure 3:
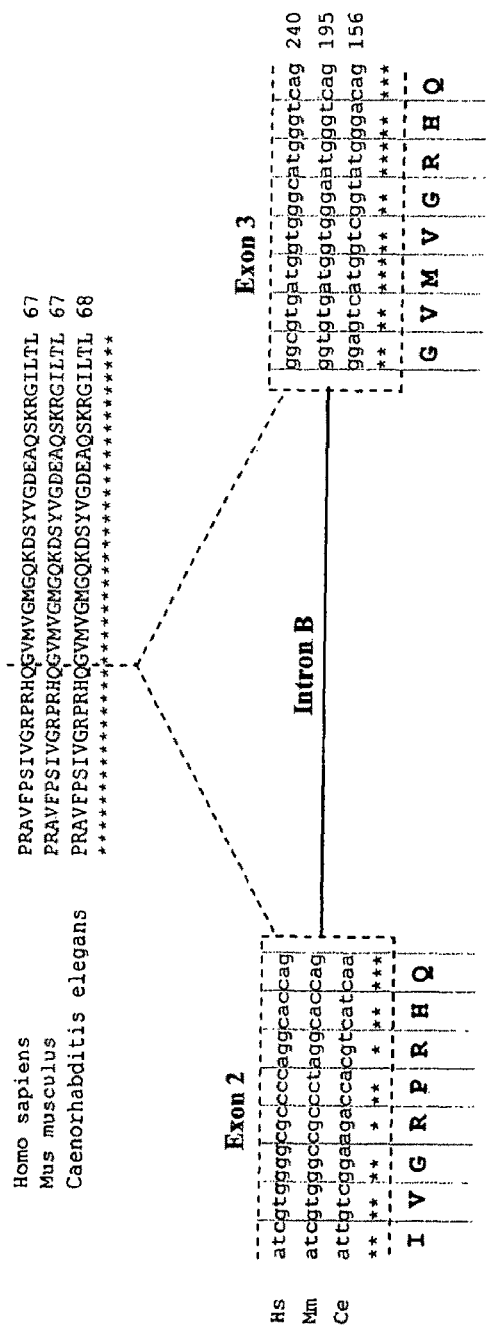
FIG. 3 Top of the figure: shows the partial amino acid sequence of the cytoplasmic beta-actin protein of three different species, *Homo sapiens* (man), *Mus musculus* (mouse) and *Caenorhabditis elegans* (nematode). The alignment between these sequences shows the high degree of conservation of the cytoplasmic beta-actin protein between species. The asterisks indicate 100% equivalence in that position between the species being compared. The numbering corresponds to the last amino acid shown according to the reference sequence in the GeneBank (refs: Hs: X00351. Mm: NM 007393.1. Ce: NM 073416.1). Middle of the figure: specifies the nucleotide sequence of the ends of exons 2 and 3 that flank intron B (W region) in said species. The exons show the nucleotide sequence in the three species being compared, divided into their corresponding codons and the amino acid residue that they code is shown below. The asterisks correspond to the nucleotide positions that are 100% conserved between the species being compared. Bottom of the figure: specifies the complete nucleotide sequence of intron B (divergent W region) in the three species being compared (SEQ ID NO:10, SEQ ID NO:11, and SEQ ID NO:12 for Hs, Mm and Ce, respectively), to illustrate the divergence used for the identification of the species in this invention.

The genome DNA obtained was then amplified by PCR. The W region (FIG. 1) was amplified with the primers designed against nucleotide positions 1132-1151 forward primer, 5'T000GCATGTGCAAGGCCGG3', SEQ ID NO: 1) and 1474-1454 reverse primer, 5'CTCCATGTCGTC-CCAGTTGG3', SEQ ID NO: 2), in accordance with human sequence M10277. The PCR conditions were as follows: standard reagents, initial denaturation step at 94° C. 3 minutes followed by 35 cycles of two steps each at 94° C. 10 seconds and 68° C. 2 minutes.

First Approximation: identification by Molecular Weight

Figure 4:
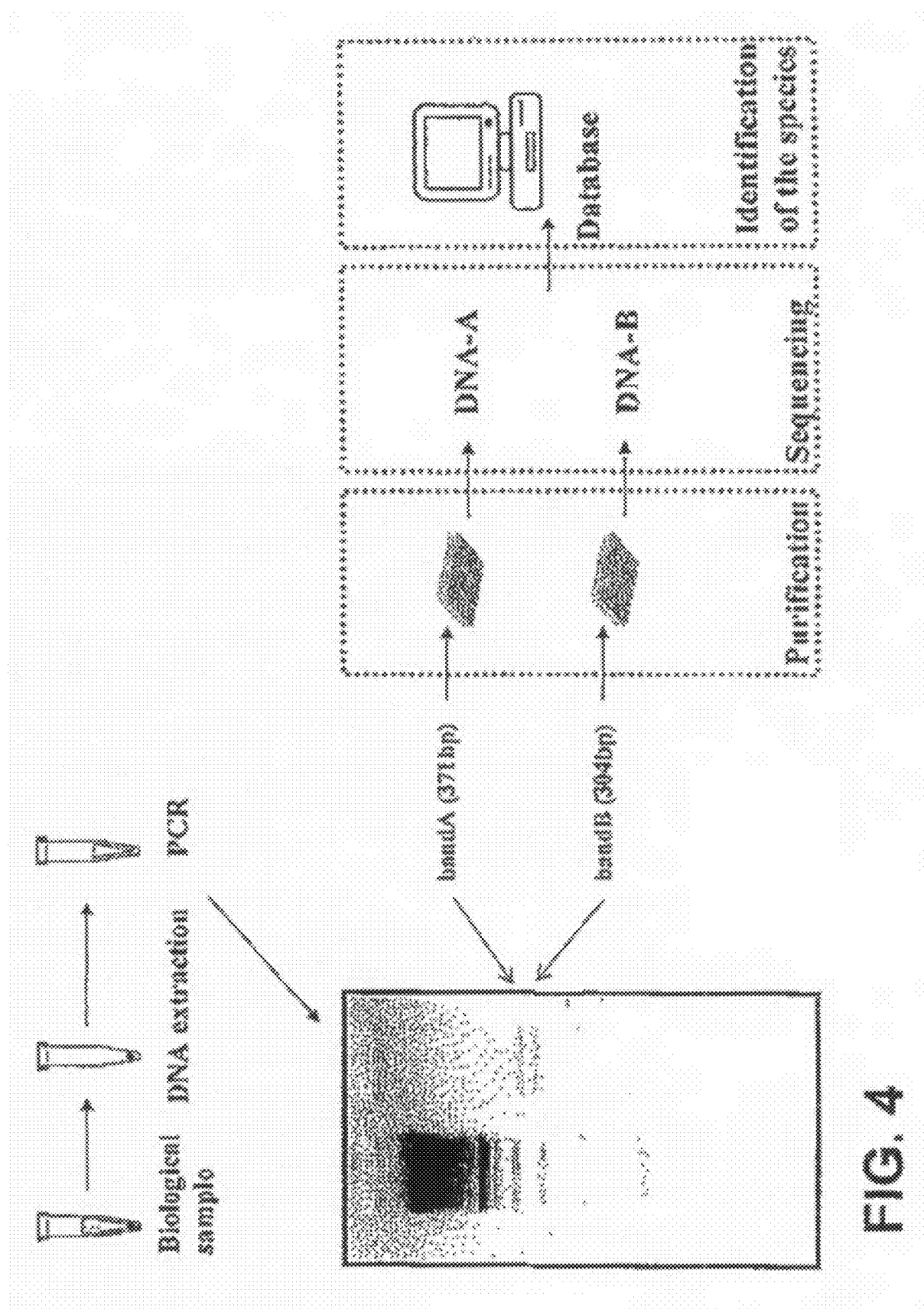
FIG. 4 shows a diagram that illustrates the process of taxonomic identification proposed in this invention, using a biologically heterogeneous mixture. The biological sample is processed to extract the DNA and subject it to amplification by PCR. In the case that is illustrated here, the W region with primers SEQ ID NO: 1 and SEQ ID NO: 2 is amplified. The PCR result is viewed using standard agarose gel electrophoresis (see electrophoresis gel, left-hand lane: molecular weight marker, 100 by ladder. Right-hand lane: bands (A and B, with approximate molecular weight expressed in base pairs bp, resulting from the PCR of the biological sample). The bands are isolated from the gel and are purified prior to undergoing DNA sequencing by standard methods. The DNA sequences obtained from each of the bands are used to interrogate a computer database that includes the sequences of the W region of biological species. The comparison of the sequences obtained using the existing sequences in the database gives the result of the identification of the species (or species) contained in the biological sample of origin.

The PCR result was viewed by standard horizontal agarose gel electrophoresis at 3% in TBE buffer. The bands that were obtained were compared with an Invitrogen 100 by ladder-marker molecular weight standard. FIG. 4 shows the results that were obtained. The comparison of the mobility of the fragments amplified in the gel using the molecular weight marker shows a molecular weight of approximately 371 and 304 base pairs. If the molecular weights of the bands obtained are compared with a database of molecular sizes obtained a priori, it is possible to make a first approximation in identifying the species present in the starting sample. FIG. 7 shows a pool of ten separate amplifications by PCR of the W region that lies between primers SEQ ID NO: 1 and SEQ ID NO: 2 of peripheral blood from eight different animal species. It is possible to observe the difference in molecular weight of this region between the animal species included. Oc: *Oryctolagus cuniculus*, rabbit. Cf: *Canis familiaris*, dog. Fc: *Felis catus*, cat. Us: *Ursus* species, Bear. Ec: *Equus caballus*, horse. Pt: *Pan Troglodytes*, chimpanzee. Oa: *Ovis aries*, goat. Hs: *Homo sapiens*, man. The left-hand lanes of the gel correspond to the 100 by ladder molecular weight standard (Invitrogen). In a first approximation by comparison with this database of molecular weights, the bands obtained in FIG. 4 would correspond to goat (371 by band) and horse (304 by band).

Second Approximation: Identification by DNA Sequencing

Figure 5:
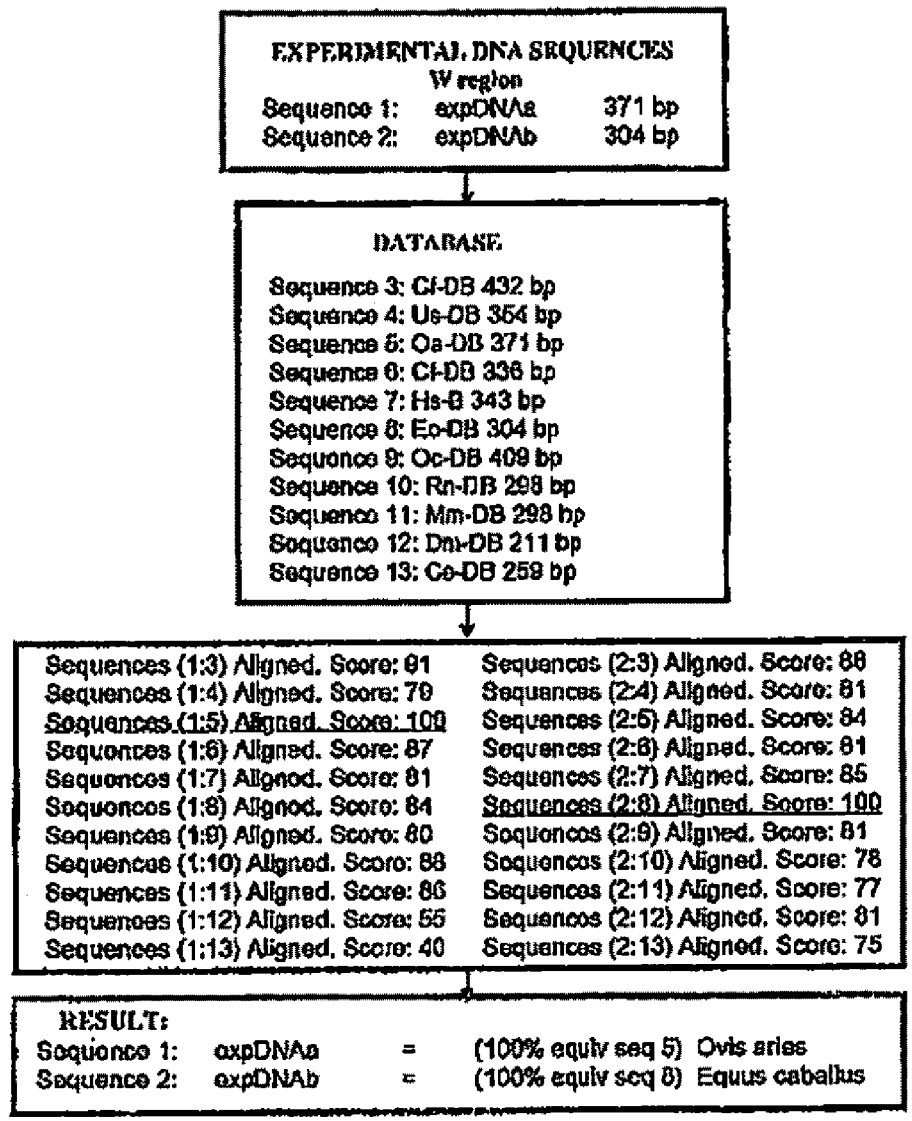
FIG. 5 shows a flow diagram illustrating the computer process for identifying the species contained in a biological sample under analysis. The DNA sequences obtained from the two fragments of the W region in the experiment shown in FIG. 4 are used to interrogate a database of DNA sequences of the W region in specific species. The database shown in this case is summarised and contains 11 different species by way of an example. (Sequence 3: Cf, *Canis familiaris*, dog. Sequence 4: Us, *Ursus* species, Bear. Sequence 5: Oa, *Ovis aries*, goat. Sequence 6: Fc, *Felis catus*, cat. Sequence 7: Hs, *Homo sapiens*, man. Sequence 8: Ec, *Equus caballus*, horse. Sequence 9: Oc, *Oryctolagus cuniculus*, rabbit. Sequence 10: Rn, *Rattus norvegicus*, rat. Sequence 11: Mm, *Mus musculus*, mouse. Sequence 12: Dm, *Drosophila melanogaster*, vinegar fly. Sequence 13: Ce, *Caenorhabditis elegans*, nematode). The resulting comparisons with 100% equivalence, which in this case are 1:5 and 2:8, show identity with the sequences included on the database and confirm that the biological sample of origin derives from a mixture of goat and horse.
Figure 6:
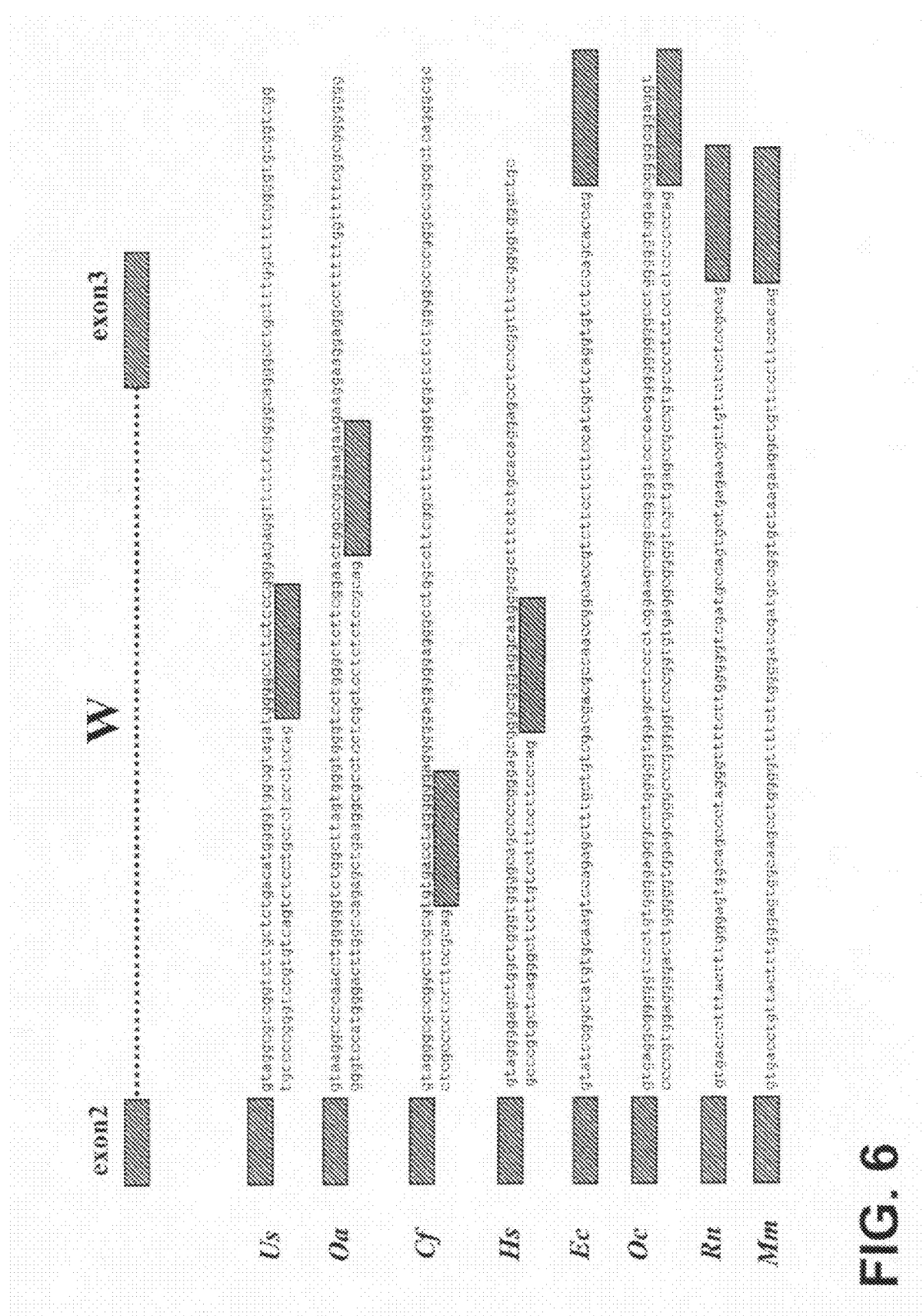
FIG. 6 shows an illustration of the divergence in molecular weight and in nucleotide sequence of the W region of some of the biological species included on the database. Us, *Ursus* species (SEQ ID NO:13). Oa, *Ovis aries* (SEQ ID NO:14).

A second approximation then identifies the two bands obtained by sequencing their DNA. The bands were purified using Life Technologies' Concert Rapid PCR Purification System kit, so that their DNA could then be sequenced. The sequencing was performed cyclically in both directions with the same primers used in the initial PCR in accordance with the protocols and reagents of Applied Biosystems' ABI-Prism 310 automatic sequencing system. The two sequences that were obtained were used to interrogate a database of DNA sequences of the W region of the cytoplasmic beta-actin gene of several species using the ClustalW program developed by the European Bioinformatic Institute of the EMBL (www.ebi.ac.uk) or an equivalent program that is available on the Internet (FIG. 5). The comparisons resulted in a 100% equivalence of 1:5 and 2:8 in this case, confirming the source of the biological sample of origin, a mixture of goat and horse.

The invention claimed is:

1. A method for genetic identification of biological species using a sample of biological material derived from a single species or from a heterogeneous mixture of species and/or subspecies, characterised in that it comprises:

(a) DNA extraction from the sample;

(b) amplification of a region of the DNA of the sample, said region corresponding to the region between positions 1130 and 1473 of the human cytoplasmic beta-actin gene, said position numbers being relative to SEQ ID NO:9, wherein (to be changed) primers hybridize to conserved sequences between positions 1130 and 1473 of SEQ ID NO:9;

(c) analysis of the amplified region to determine the size in base-pairs and/or the precise DNA sequence thereof; and (d) taxonomic identification of the biological species or subspecies from which the sample was derived by comparison of the size and/or DNA sequence of said amplified region with a database containing pre-established sizes and/or DNA sequences of the corresponding region of the cytoplasmic beta-actin gene of a plurality of species and/or subspecies.

2. The method of claim 1, characterised in that in the amplification step gene segments of evolutionarily divergent regions of the cytoplasmic beta-actin gene are amplified using DNA oligonucleotide primers corresponding to ranges of nucleotide positions in SEQ ID NO:9 having greater than 98% sequence identity among the species and sub-species present in the database.

3. The method of claim 1, characterised in that in the amplification step the segments to be amplified comprise the whole intronic DNA sequence and at least a portion of the flanking exonic sequences relative to SEQ ID NO:9.

4. The method of claim 1, characterised in that in the amplification step primers are used that hybridize with one or more sequences within the regions between positions 1130 to 1191 and 1453 to 1473 of the cytoplasmic beta-actin gene.

5. The method of claim 4, characterised in that the primers used in the amplification step are 5'TCCGGCATGTGCAAGGCCGG3' (SEQ ID NO:1) and 5'CTCCATGTCGTCCCAGTTGG3' (SEQ ID NO: 2).

6. The method of claim 1, characterised in that the sample is taken from horse, goat, rabbit, dog, cat, chimpanzee, human or brown bear tissue.

* * * * *

SEQUENCE LISTING

<160> NUMBER OF SEQ ID NOS: 18

<210> SEQ ID NO 1
<211> LENGTH: 20
<212> TYPE: DNA
<213> ORGANISM: Homo sapiens

<400> SEQUENCE: 1
tccggcatgt gcaaggccgg          20

<210> SEQ ID NO 2
<211> LENGTH: 20
<212> TYPE: DNA

-continued

<213> ORGANISM: Homo sapiens

<400> SEQUENCE: 2
ctccatgtcg tcccagttgg                                           20

<210> SEQ ID NO 3
<211> LENGTH: 31
<212> TYPE: DNA
<213> ORGANISM: Homo sapiens

<400> SEQUENCE: 3
accaactggg acgacatgga gaagatctgg c                              31

<210> SEQ ID NO 4
<211> LENGTH: 30
<212> TYPE: DNA
<213> ORGANISM: Homo sapiens
<220> FEATURE:
<221> NAME/KEY: modified_base
<222> LOCATION: (9)..(9)
<223> OTHER INFORMATION: a, c, g, t, unknown or other

<400> SEQUENCE: 4
tacatggcng gggtgttaaa ggtctcaaac                                30

<210> SEQ ID NO 5
<211> LENGTH: 30
<212> TYPE: DNA
<213> ORGANISM: Homo sapiens

<400> SEQUENCE: 5
tgccctgagg ccctcttcca gccttccttc                                30

<210> SEQ ID NO 6
<211> LENGTH: 38
<212> TYPE: DNA
<213> ORGANISM: Homo sapiens
<220> FEATURE:
<221> NAME/KEY: modified_base
<222> LOCATION: (30)..(30)
<223> OTHER INFORMATION: a, c, g, t, unknown or other

<400> SEQUENCE: 6
gggtacatgg tggtgccgcc agacagcacn gtgttggc                       38

<210> SEQ ID NO 7
<211> LENGTH: 38
<212> TYPE: DNA
<213> ORGANISM: Homo sapiens
<220> FEATURE:
<221> NAME/KEY: modified_base
<222> LOCATION: (9)..(9)
<223> OTHER INFORMATION: a, c, g, t, unknown or other

<400> SEQUENCE: 7
gccaacacng tgctgtctgg cggcaccacc atgtaccc                       38

<210> SEQ ID NO 8
<211> LENGTH: 29
<212> TYPE: DNA
<213> ORGANISM: Homo sapiens

<400> SEQUENCE: 8
tcgtactcct gcttgctgat ccacatctg                                 29

<210> SEQ ID NO 9
<211> LENGTH: 3646
<212> TYPE: DNA
<213> ORGANISM: Homo sapiens

<400> SEQUENCE: 9

| | | | | | |
|---|---|---|---|---|---|
| gcccagcacc | ccaaggcggc | caacgccaaa | actctccctc | ctcctcttcc | tcaatctcgc | 60 |
| tctcgctctt | tttttttttc | gcaaaaggag | gggagagggg | gtaaaaaaat | gctgcactgt | 120 |
| gcggcgaagc | cggtgagtga | gcggcgcggg | gccaatcagc | gtgcgccgtt | ccgaaagttg | 180 |
| cctttttatgg | ctcgagcggc | cgcggcgcg | ccctataaaa | cccagcggcg | cgacgcgcca | 240 |
| ccaccgccga | gaccgcgtcc | gcccgcgagc | acagagcctc | gcctttgccg | atccgccgcc | 300 |
| cgtccacacc | cgccgccagg | taagcccggc | cagccgaccg | gggcatgcgg | ccgcggccct | 360 |
| tcgcccgtgc | agagccgccg | tctgggccgc | agcgggggc | gcatgggcg | gaaccggacc | 420 |
| gccgtggggg | gcgcgggaga | agccctgggc | cctccggaga | tggggacac | ccacgccag | 480 |
| ttcgcaggcg | cgaggccgcg | ctcgggcggg | cgcgctccgg | gggtgccgct | ctcggggcgg | 540 |
| gggcaaccgg | cggggtcttt | gtctgagccg | ggctcttgcc | aatggggatc | gcacggtggg | 600 |
| cgcggcgtag | ccccgtcag | gcccggtggg | ggctggggcg | ccatgcgcgt | gcgcgctggt | 660 |
| cctttgggcg | ctaactgcgt | gcgcgctggg | aattggcgct | aattgcgcgt | gcgcgctggg | 720 |
| actcaatggc | gctaatcgcg | cgtgcgttct | ggggcccggg | cgcttgcgcc | acttcctgcc | 780 |
| cgagccgctg | gcgcccgagg | gtgtggccgt | gcgtgcgcg | cgcgcgaccc | ggtcgctgtt | 840 |
| tgaaccgggc | ggaggcgggg | ctggcgcccg | gttgggaggg | ggttggggcc | tggcttcctg | 900 |
| ccgcgcgccg | cggggacgcc | tccgaccagt | gtttgccttt | tatggtaata | acgcggccgg | 960 |
| cccggcttcc | tttgtcccca | atctgggcgc | gcgccggcgc | ccctggcgg | cctaaggact | 1020 |
| cggcgcgccg | gaagtggcca | gggcggggc | gacttcggct | cacagcgcgc | ccggctattc | 1080 |
| tcgcagctca | ccatggatga | tgatatcgcc | gcgctcgtcg | tcgacaacgg | ctccggcatg | 1140 |
| tgcaaggccg | gcttcgcggg | cgacgatgcc | ccccgggccg | tcttcccctc | catcgtgggg | 1200 |
| cgccccaggc | accaggtagg | ggagctggct | gggtggggca | gccccgggag | cgggcgggag | 1260 |
| gcaagggcgc | tttctctgca | caggagcctc | ccggtttccg | gggtgggctg | cgcccgtgct | 1320 |
| cagggcttct | tgtcctttcc | ttcccagggc | gtgatggtgg | gcatgggtca | gaaggattcc | 1380 |
| tatgtgggcg | acgaggccca | gagcaagaga | ggcatcctca | ccctgaagta | ccccatcgag | 1440 |
| cacggcatcg | tcaccaactg | ggacgacatg | gagaaaatct | ggcaccacac | cttctacaat | 1500 |
| gagctgcgtg | tggctcccga | ggagcacccc | gtgctgctga | ccgaggcccc | cctgaacccc | 1560 |
| aaggccaacc | gcgagaagat | gacccaggtg | agtggcccgc | tacctcttct | ggtgccgcc | 1620 |
| tccctccttc | ctggcctccc | ggagctgcgc | cctttctcac | tggttctctc | ttctgccgtt | 1680 |
| ttccgtagga | ctctcttctc | tgacctgagt | ctccttgga | actctgcagg | ttctatttgc | 1740 |
| tttttcccag | atgagctctt | tttctggtgt | ttgtctctct | gactaggtgt | ctgagacagt | 1800 |
| gttgtgggtg | taggtactaa | cactggctcg | tgtgacaagg | ccatgaggct | ggtgtaaagc | 1860 |
| ggccttggag | tgtgtattaa | gtaggcgcac | agtaggtctg | aacagactcc | ccatcccaag | 1920 |
| accccagcac | acttagccgt | gttctttgca | ctttctgcat | gtccccgtc | tggcctggct | 1980 |
| gtccccagtg | gcttccccag | tgtgacatgg | tgcatctctg | ccttacagat | catgtttgag | 2040 |
| accttcaaca | cccagccat | gtacgttgct | atccaggctg | tgctatccct | gtacgcctct | 2100 |
| ggccgtacca | ctggcatcgt | gatggactcc | ggtgacgggg | tcacccacac | tgtgcccatc | 2160 |

```
tacgaggggt atgccctccc ccatgccatc ctgcgtctgg acctggctgg ccgggacctg    2220
actgactacc tcatgaagat cctcaccgag cgcggctaca gcttcaccac cacggccgag    2280
cgggaaatcg tgcgtgacat taaggagaag ctgtgctacg tcgccctgga cttcgagcaa    2340
gagatggcca cggctgcttc cagctcctcc ctggagaaga gctacgagct gcctgacggc    2400
caggtcatca ccattggcaa tgagcggttc cgctgccctg aggcactctt ccagccttcc    2460
ttcctgggtg agtggagact gtctcccggc tctgcctgac atgagggtta ccctcgggg    2520 ctgtgctgtg aagctaagt cctgccctca tttccctctc aggcatggag tcctgtggca    2580
tccacgaaac taccttcaac tccatcatga agtgtgacgt ggacatccgc aaagacctgt    2640
acgccaacac agtgctgtct ggcggcacca ccatgtaccc tggcattgcc gacaggatgc    2700
agaaggagat cactgccctg gcacccagca caatgaagat caaggtgggt gtctttcctg    2760
cctgagctga cctgggcagg tcagctgtgg ggtcctgtgg tgtgtgggga gctgtcacat    2820
ccagggtcct cactgcctgt ccccttccct cctcagatca ttgctcctcc tgagcgcaag    2880
tactccgtgt ggatcggcgg ctccatcctg gcctcgctgt ccaccttcca gcagatgtgg    2940
atcagcaagc aggagtatga cgagtccggc ccctccatcg tccaccgcaa atgcttctag    3000
gcggactatg acttagttgc gttacaccct tcttgacaa aacctaactt gcgcagaaaa    3060
caagatgaga ttggcatggc tttatttgtt tttttgttt tgtttggtt ttttttttt    3120 ttttggcttg actcaggatt taaaaactgg aacggtgaag gtgacagcag tcggttggag    3180
cgagcatccc ccaaagttca aatgtggcc gaggactttg attgcattgt tgttttttta    3240
atagtcattc caaatatgag atgcattgtt acaggaagtc ccttgccatc ctaaaagcca    3300
ccccacttct ctctaaggag aatggcccag tcctctccca agtccacaca ggggaggtga    3360
tagcattgct ttcgtgtaaa ttatgtaatg caaaatttt ttaatcttcg ccttaatact    3420
tttttatttt gttttatttt gaatgatgag ccttcgtgcc cccccttccc ccttttgtc    3480 ccccaacttg agatgtatga aggcttttgg tctccctggg agtgggtgga ggcagccagg    3540
gcttacctgt acactgactt gagaccagtt gaataaaagt gcacaccta aaaatgaggc    3600 caagtgtgac tttgtggtgt ggctgggttg ggggcagcag agggtg          3646

<210> SEQ ID NO 10
<211> LENGTH: 179
<212> TYPE: DNA
<213> ORGANISM: Homo sapiens

<400> SEQUENCE: 10
atcgtggggc gccccaggca ccaggtaggg gagctggctg ggtggggcag ccccgggagc      60
gggcgggagg caagggcgct ttctctgcac aggagcctcc cggtttccgg ggtgggctgc     120
gcccgtgctc agggcttctt gcctttcctt cccagggcgt gatggtgggc atgggtcag     179

<210> SEQ ID NO 11
<211> LENGTH: 135
<212> TYPE: DNA
<213> ORGANISM: Mus musculus

<400> SEQUENCE: 11
atcgtgggcc gccctaggca ccaggtaagt gacctgttgg cactttggga gtaagcctgg      60
ggttttcttg gggatcgatg ccggtgctaa gaaggctgtt cccttccaca gggtgtgatg     120
gtgggaatgg gtcag                                                     135
```

```
<210> SEQ ID NO 12
<211> LENGTH: 99
<212> TYPE: DNA
<213> ORGANISM: Caenorhabditis elegans

<400> SEQUENCE: 12
attgtcggaa gaccacgtca tcaaggtaaa taattaatac attcgatgat taaatttatg      60
cgtactattt caggaggagt catggtcggt atgggacag                             99

<210> SEQ ID NO 13
<211> LENGTH: 141
<212> TYPE: DNA
<213> ORGANISM: Ursus sp.

<400> SEQUENCE: 13
gtaggcgccg gtcttgctct gacatggggt ggcgtagatg gggccttctc ccgggagagg      60
ttctctcggg gcagggcctg ctttggcttt cggggtgcgg tcggtgcccc gggtccgtgt     120
cagtctcctg ccctcctcca g                                               141

<210> SEQ ID NO 14
<211> LENGTH: 163
<212> TYPE: DNA
<213> ORGANISM: Ovis aries

<400> SEQUENCE: 14
gtaaggcccc aacctggggg tctggcttag tgggtgggtc ctggactctt cggagctggc      60
ggggaggagg agggagggag gccttttttgg ttttctgggt ggggaggggg gtcggtggga    120
cttggccaaa gctgaaggcg cctcctcgct cctctctccg cag                       163

<210> SEQ ID NO 15
<211> LENGTH: 125
<212> TYPE: DNA
<213> ORGANISM: Canis familiaris

<400> SEQUENCE: 15
gtagggcgcc ggcctcgcgt gtgacctggg gggaggggga ggggagggc ctggccttcg       60 gctttcgggg tggctctctg ggcccccggg cccgcgctca gggcgcctcg ccctccttc     120 cgcag                                                                125

<210> SEQ ID NO 16
<211> LENGTH: 94
<212> TYPE: DNA
<213> ORGANISM: Equus caballas

<400> SEQUENCE: 16
gtatccggct atgtgcaagt ccagagcttt gctgtcgacg acgccaaccg gcaccgtctt      60
cctcttccat cccgctcagg tgctccagca ccag                                 94

<210> SEQ ID NO 17
<211> LENGTH: 198
<212> TYPE: DNA
<213> ORGANISM: Oryctolagus cuniculus

<400> SEQUENCE: 17
gtgaggcggg ggtccctgtg gggagggcct gggggtggag cctcccctcg gaagcgggcg      60
ggggtcccca cgggggggg cctgggggtg agcggggcg gaggtccccg tggagggggac    120 ctgggggtgg agcggggccg gggtccgg tgtgaggcgg ggtcgctgag ccgccgtgcc      180
```

```
cctctcctct cccccag                                                198
```

<210> SEQ ID NO 18
<211> LENGTH: 83
<212> TYPE: DNA
<213> ORGANISM: Rattus norvegicus

<400> SEQUENCE: 18

```
gtgaccctttt actttgggag tggcagccct agggtttct tgggggtcga tgccagtgct    60
gagaacgttg ttctcctccg cag                                            83
```